United States Patent [19]

Shih et al.

[11] Patent Number: 5,710,280

[45] Date of Patent: Jan. 20, 1998

[54] PREPARATION OF FLUCONAZOLE AND PHARMACEUTICALLY ACCEPTABLE SALTS THEREOF

[75] Inventors: Kae-Shyang Shih; Lie-Rong Chen; Ching-Wei Liu; Chia-Lin J. Wang, all of Taipei, Taiwan

[73] Assignee: Development Center for Biotechnology, Taiwan

[21] Appl. No.: 679,457

[22] Filed: Jul. 9, 1996

[51] Int. Cl.$^6$ .................................................. C07D 249/08
[52] U.S. Cl. ........................................................ 548/266.6
[58] Field of Search ............................................. 548/266.6

[56] References Cited

U.S. PATENT DOCUMENTS 4,404,216   9/1983   Richardson .

Primary Examiner—Patricia L. Morris
Attorney, Agent, or Firm—Fish & Richardson P.C.

[57] ABSTRACT

A process for preparing fluconazole, including the steps of (1) acylating 1,3-difluorobenzene (DFB) to obtain 2-chloro-2',4'-difluoroacetophenone (CAP); (2) alkylating 4-amino-4H-1,2,4-triazole (4-AT) with CAP to obtain 2-(1H-1,2,4-triazol-1-yl)-2',4'-difluoroacetophenone (TAAP) salt; (3) deaminating TAAP salt to obtain TAAP; and (4) reacting TAAP with 1,2,4-triazole to obtain fluconazole.

20 Claims, No Drawings

PREPARATION OF FLUCONAZOLE AND PHARMACEUTICALLY ACCEPTABLE SALTS THEREOF

BACKGROUND OF THE INVENTION

Fluconazole, i.e., 2-(2,4-difluorophenyl)-1,3-bis(1H-1,2,4-triazol-1-yl)propan-2-ol, is an antifungal agent developed by Pfizer Inc. The compound is useful for treating various fungal infections such as mycohemia, mycosis (both in the respiratory system and digestive system), and fungal meningitis, which are caused by, among others, various species of Candida, Coccidioides and Trichophyton. Fluconazole inhibits the biosynthesis of ergosterol, an important component of fungal cell membrane. The inhibition is highly specific to ergosterol biosynthesis in fungi.

A method of preparing fluconazole can be found in U.S. Pat. No. 4,404,216 (1983).

SUMMARY OF THE INVENTION

The present invention features an improved process of preparing fluconazole. The process includes the following steps:

(1) acylating 1,3-difluorobenzene (DFB), e.g., with a chloroacetyl halide, to obtain 2-chloro-2',4'-difluoroacetophenone (CAP), preferably with aluminum trichloride as the catalyst and dichloromethane as the solvent.

(2) alkylating 4-amino-4H-1,2,4-triazole (4-AT) with CAP to obtain 2-(1H-1,2,4-triazol-1-yl)-2',4'-difluoroacetophenone (TAAP) salt;

(3) deaminating TAAP salt, e.g., with an acid such as diluted hydrochloric acid, to obtain TAAP; and (4) reacting TAAP with 1,2,4-triazole (TA) to obtain fluconazole, preferably in an aqueous solvent (e.g., water) which contains a strong base (e.g., KOH).

Other features or advantages of the present invention will be apparent from the following detailed description of the invention, and also from the appending claims.

DETAILED DESCRIPTION OF THE INVENTION

It is believed that one skilled in the art can, based on the description herein, utilize the present invention to its fullest extent. The following specific example, as shown in Scheme A, is therefore to be construed as merely illustrative, and not limitative of the remainder of the disclosure in any way whatsoever. Furthermore, U.S. Pat. No. 4,404,216 cited above is incorporated by reference in its entirety.

Scheme A

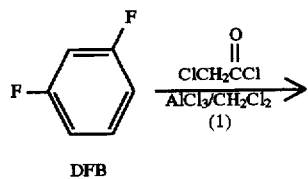

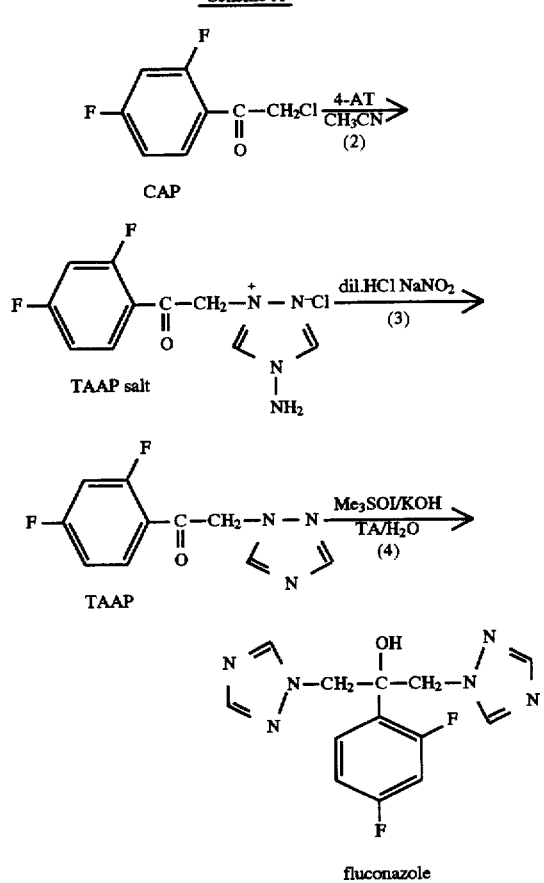

fluconazole

More details regarding the process depicted in Scheme A, which includes 4 steps, are provided below:

Step (1) is Friedel-Crafts acylation, which can be conducted using DFB and chloroacetyl chloride as the starting materials in the presence of a catalyst such as aluminum trichloride. An organic solvent such as dichloromethane is added to the reaction mixture to slowly reduce the heat emitted during the reaction. CAP can be produced at a yield of about 97% or higher and the crude product can be used in the subsequent nitrogen alkylation reaction without further purification.

Step (2) involves reacting 4-AT with CAP in the presence of a suitable solvent such as acetonitrile. The yield of TAAP salt, obtained after filtration, can be as high as about 95%. 4-AT is used as the starting material of this step to avoid any isomerization during the reaction.

In step (3), the TAAP salt obtained from step (2) is subjected to deamination with an acid and sodium nitrite. The yeild of free TAAP thus obtained after precipitation and filtration can be about 85% or higher. The acid used in the step can be a diluted hydrochloric acid solution, for example, 1.5 N hydrochloric acid.

In step (4), fluconazole is obtained in a single-step epoxidation/ring-opening reaction. The yield can reach about 50% or greater. More specifically, the reaction of TAAP, TA, and trimethyl sulfoxonium iodide (Me₃SOI) can be conducted in a basic aqueous solution at a temperature of about 40°–100° C. (e.g., about 60°–80° C. or about 70° C.) for about 3–20 hours (e.g., 12–18 hours or about 16 hours). Both aqueous solvents and other aprotonic solvents such as N,N-dimethylformamide, dimethyl sulfoxide, and hexamethylphosphoramide can be used. Examples of a suitable base include, but are not limited to, sodium hydroxide, potassium hydroxide, sodium carbonate, and potassium carbonate.

The pharmaceutically acceptable salts of fluconazole prepared by the above-described process are preferably the acid addition salts. Pharmaceutically acceptable acid addition salts can be formed from acids such as hydrochloric, hydrobromic, phosphoric, sulfuric, maleic, citric, acetic, tartaric, succinic, oxalic, malic, glutamic, and the like. These salts may be obtained by using conventional procedures such as, for example, by mixing solutions containing equimolar amounts of the free base of fluconazole and the desired acid together, followed by filtration to collect the required salts, if insoluble, or else by evaporation of the solvent from the system in accordance with standard techniques.

The following actual example further illustrates the present invention without limiting its scope. Any modification and substitution easily recognized by persons skilled in the art are within the scope and the spirit of the present invention.

(1) Preparation of CAP 141.1 g of aluminum trichloride was first added to 86 ml of DFB and 77 ml of chloroacetyl chloride was then added to the mixture, which was allowed to react at 60° C. for 3 hours. After the reaction mixture had cooled down, 500 g of cold water was added to it. The mixture was stirred for about 20 minutes and then filtered to afford about 158.5 g of CAP in solid form (91% yield). $^1$H-NMR data ($CDCL_3$ $\delta$ values) of the product:

$\delta$ 4.69 (2H, s)

$\delta$ 6.96 (2H, m)

$\delta$ 8.05 (1H, m)

(2) Preparation of TAAP Salt

A solution of 158.5 g of CAP and 88.8 g of 4-AT in 1,600 ml of cyanomethane was heated at reflux for 16 hours, cooled down, and filtered. The solid thus obtained was then washed with 500 ml of ethyl ether once to afford $TAAP^+Cl^-$. $^1$H-NMR data ($CD_3OD$, $\delta$ values) of the product:

$\delta$ 6.02 (2H, s)

$\delta$ 7.22 (2H, m)

$\delta$ 8.12 (1H, m)

$\delta$ 9.04 (1H, s)

(3) Preparation of TAAP

The crude product obtained above was dissolved in 1,320 ml of 1.5 N hydrochloric acid. To the solution thus obtained, an aqueous solution (330 ml) of sodium nitrite (58.2 g) was dropwise added and the mixture was allowed to react for 30 minutes. Aqueous ammonium was then used to adjust the reaction mixture to a neutral pH. The solid was precipitated and filtered to afford 159 g of crude TAAP (yield about 80%), which had a water content of about 10%. $^1$H-NMR data ($CDCl_3$, $\delta$ values) of the product:

$\delta$ 5.58 (2H, d)

$\delta$ 7.03 (2H, m)

$\delta$ 7.29 (1H, m)

$\delta$ 7.98 (1H, s)

$\delta$ 8.21 (1H, s)

(4) Preparation of Fluconazole 34 g of TA, 57.87 g of potassium hydroxide, 118 g of trimethyl sulfoxonium iodide, and 100 g of TAAP were dissolved in 1,600 ml of water to obtain an aqueous solution. The aqueous solution was heated at 70° C. to react for 16 hours. Upon the completion of the reaction, the solution was adjusted with 4 N hydrochloric acid to a neutral pH and then extracted with acetyl acetate (800 ml×3). The organic layer was collected, dried with 30 g of anhydrous calcium dichloride, decolorized with 15 g of active charcoal, and finally filtered off solid residues. The filtrate was concentrated to afford 99.3 g of the crude product (yield 72%). The crude product was further recrystallized from 500 ml of a solvent mixture of acetyl acetate and n-hexane (2:1) to afford 66.3 g of the final product in the form of white solid (yield 48%). $^1$H-NMR data ($CD_3OD$ $\delta$ values) of the product:

$\delta$ 4.68 (4H, dd)

$\delta$ 6.78 (1H, m)

$\delta$ 6.97 (1H, m)

$\delta$ 7.19 (1H, m)

$\delta$ 7.81 (1H, s)

$\delta$ 8.33 (1H, s)

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A process for preparing 2-(2,4-difluorophenyl)-1,3-bis-(1H-1,2,4-triazol-1-yl)propan-2-ol, said process comprising (1) acylating 1,3-difluorobenzene (DFB) to obtain 2-chloro-2',4'-difluoroacetophenone (CAP);

(2) alkylating 4-amino-4H-1,2,4-triazole (4-AT) with CAP to obtain 2-(1H-1,2,4-triazol-1-yl)-2',4'-difluoroacetophenone (TAAP) salt;

(3) deaminating TAAP salt to obtain TAAP; and (4) reacting TAAP with 1,2,4-triazole to obtain fluconazole.

2. The process of claim 1, wherein said step (1) is conducted by acylating DFB with chloroacetyl halide.

3. The process of claim 1, wherein said step (3) is conducted by deaminating TAAP salt with an acid.

4. The process of claim 2, wherein said step (3) is conducted by deaminating TAAP salt with an acid.

5. The process of claim 2, wherein chloroacetyl halide is chloroacetyl chloride.

6. The process of claim 3, wherein chloroacetyl halide is chloroacetyl chloride.

7. The process of claim 4, wherein chloroacetyl halide is chloroacetyl chloride.

8. The process of claim 1, wherein said step (4) is conducted in an aqueous solvent which contains a strong base.

9. The process of claim 2, wherein said step (4) is conducted in an aqueous solvent which contains a strong base.

10. The process of claim 3, wherein said step (4) is conducted in an aqueous solvent which contains a strong base.

11. The process of claim 4, wherein said step (4) is conducted in an aqueous solvent which contains a strong base.

12. The process of claim 5, wherein said step (4) is conducted in an aqueous solvent which contains a strong base.

13. The process of claim 6, wherein said step (4) is conducted in an aqueous solvent which contains a strong base.

14. The process of claim 7, wherein said step (4) is conducted in an aqueous solvent which contains a strong base.

15. The process of claim 5, wherein said step (1) is conducted with aluminum trichloride as the catalyst and dichloromethane as the solvent.

16. The process of claim 6, wherein said step (1) is conducted with aluminum trichloride as the catalyst and dichloromethane as the solvent.

17. The process of claim 7, wherein said step (1) is conducted with aluminum trichloride as the catalyst and dichloromethane as the solvent.

18. The process of claim 14, wherein said step (1) is conducted with aluminum trichloride as the catalyst and dichloromethane as the solvent.

19. The process of claim 14, wherein said acid used in step (3) is diluted hydrochloric acid.

20. The process of claim 14, wherein said aqueous solvent used in step (4) is water.

* * * * *